United States Patent [19]

Richardson et al.

[11] Patent Number: 4,618,616

[45] Date of Patent: Oct. 21, 1986

[54] CYCLOPROPYLIDENE ANTIFUNGAL AGENTS

[75] Inventors: Kenneth Richardson, Canterbury; Robert J. Bass, Birchington; Kelvin Cooper, Ramsgate, all of England

[73] Assignee: Pfizer Inc., New York, N.Y.

[21] Appl. No.: 738,143

[22] Filed: May 24, 1985

[30] Foreign Application Priority Data

Jun. 7, 1984 [GB] United Kingdom ............... 8414519

[51] Int. Cl.$^4$ ............... A01N 43/653; C07D 249/08
[52] U.S. Cl. ................... 514/340; 514/383; 546/276; 548/262
[58] Field of Search ............ 548/262; 546/276; 514/340, 383

[56] References Cited

U.S. PATENT DOCUMENTS 4,560,697 12/1985 Richardson et al. ............... 514/383
4,575,517 3/1986 Krüger et al. ...................... 514/383

FOREIGN PATENT DOCUMENTS 51565 5/1982 .
2129000 5/1984 United Kingdom .

Primary Examiner—Richard L. Raymond
Attorney, Agent, or Firm—Charles J. Knuth; Albert E. Frost; James M. McManus

[57] ABSTRACT 1-substituted-1-haloaryl-1-('-[1H-1,2,4-triazol-1-yl]-cyclopropyl)-2-(1H-1,2,4-triazol-1-yl)ethane compounds and pharmaceutical compositions thereof are useful in treating fungal infections in mammals and plants.

10 Claims, No Drawings

CYCLOPROPYLIDENE ANTIFUNGAL AGENTS

BACKGROUND OF THE INVENTION

This invention relates to novel cyclopropylidene derivatives which have antifungal activity and which are useful in the treatment of fungal infections in humans as well as in plants and seeds.

U.S. Pat. No. 4,404,216 discloses 1,3-bis(1H-1,2,4-triazol-1-yl)-2-propanol derivatives as antifungal agents, as does U.S. Pat. No. 4,416,682. European Patent Application 0096569 disclose 1,3-bis(1H-1,2,4-triazol-1-yl)-2-propyl halides, while U.K. Patent Application 2,129,000A claims as antifungal agents a series of alpha-(1H-1,2,4-triazol-1-yl)methylalpha-cyclopropylbenzyl alcohols.

SUMMARY OF THE INVENTION

The compounds of the present invention are of the formula

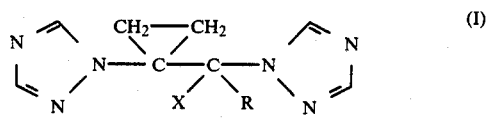

and a pharmaceutically or agriculturally acceptable salt thereof, wherein X is hydroxy or chloro and R is chlorophenyl, fluorophenyl, dichlorophenyl, difluorophenyl or 5-chloropyrid-2-yl.

A preferred group of compounds are those wherein X is hydroxy; especially preferred within the group are compounds where R is 4-chlorophenyl, 4-fluorophenyl, 2,4-dichlorophenyl or 2,4-difluorophenyl.

The invention also provides a pharmaceutical composition comprising a compound of formula (I) or a pharmaceutically acceptable salt thereof, together with a pharmaceutically acceptable diluent or carrier, and a fungicidal composition for agricultural use comprising a compound of formula (I) or an agriculturally acceptable salt thereof, together with an agriculturally acceptable diluent or carrier.

This invention further provides a method of treating a fungal infection in a plant or seed which comprises treating said plant or seed with an antifungally effective amount of an fungicidal composition as described above, and a method of treating a fungal infection in a human being which comprises administering to said human being an antifungally effective amount of a pharmaceutical composition as described above.

DETAILED DESCRIPTION OF THE INVENTION

The compounds of the formula (I) in which X is —OH can be prepared according to the following reaction scheme:

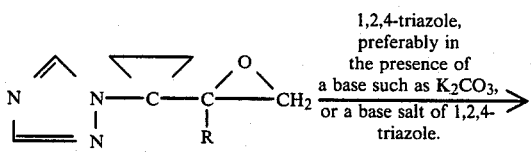

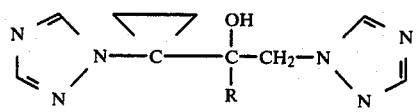

In a typical reaction, the epoxide (II), 1,2,4-triazole and anhydrous potassium carbonate are heated together at about 40°–120° C., in a suitable solvent, e.g. dimethylformamide, until the reaction is complete, usually in 1–16 hours. The product (IA) can then be isolated and purified in a conventional manner.

If a base salt of 1,2,4-triazole is used, it is preferably an alkali metal salt, e.g. a sodium or potassium salt.

There are several methods for preparing the intermediates (II). These are illustrated schematically as follows:

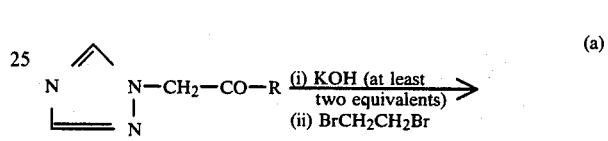

or

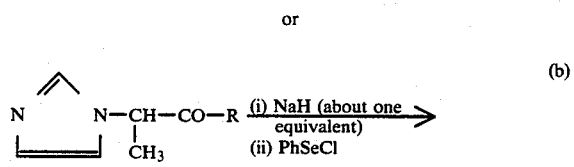

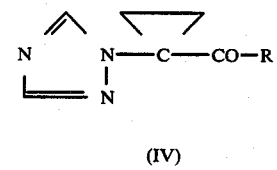

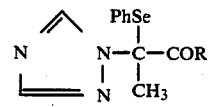

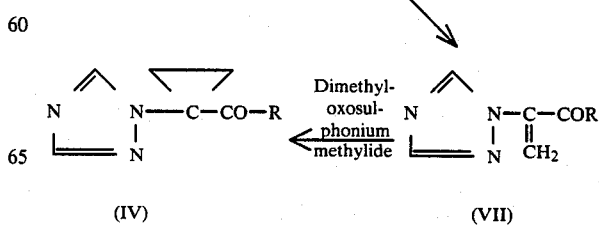

-continued

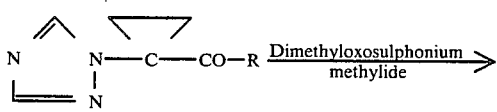

(IV)

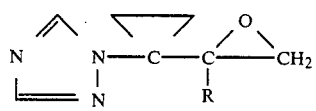

(II)

In steps (b) and (c), trimethylsulphoxonium iodide and aqueous sodium hydroxide/cetrimide can be used to generate dimethyloxosulphonium methylide in situ.

It is preferred to obtain the intermediates (II) via steps (a) and (c).

Step (a) is preferably carried out by adding "18-Crown-6-ether" (1,4,7,10,13,16-hexaoxacyclooctadecane) and potassium hydroxide (at least two equivalents) to a solution of the ketone (III) in methylene chloride.

The Crown ether solubilizes the potassium hydroxide in methylene chloride, which is a non-polar solvent. After stirring for a few minutes, 1,2-dibromoethane is added, and the reaction mixture is stirred at room temperature for up to about 24 hours. The ketone (IV) can then be isolated and purified conventionally.

Step (a) can also be carried out in a conventional manner. Typically, the ketone (IV), trimethylsulphoxonium iodide, cetrimide and aqueous sodium hydroxide are heated together, preferably under reflux, in a suitable organic solvent, e.g. 1,1,1-trichloroethane, until the reaction is complete, which is generally in 24 hours or less. The oxirane (II) can then be recovered in a conventional manner.

Step (b) is an alternative to (a) but is a more complex route. Typical experimental details are given in Preparation 1 parts (B) to (D).

The starting materials of the formula (III) are either known compounds or can be prepared by methods analogous to those known in the art (see e.g. British Patent Specifications Nos. 1512918, 1533705, 1533706 and European patent applications publication Nos. 44605, 61051 and 69442).

The starting materials of the formula (V) are described in our European patent application No. 84301670.0. They can be prepared by routine methods, typically as follows:

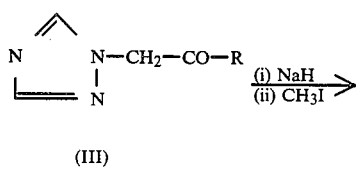

(III)

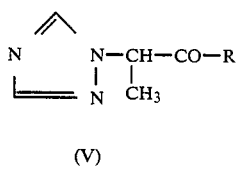

(V)

The compounds of the formula (I) in which X is Cl can be prepared by the halogenation of the corresponding compounds in which X is —OH.

The halogenation is carried out according to conventional procedures, e.g. using $SOCl_2$.

In a typical procedure utilising thionyl chloride the hydroxy-containing bis-triazole (II) in a suitable organic solvent, e.g. dry acetonitrile, is reacted with thionyl chloride or bromide at a temperature of from 0° C. to reflux temperature, optionally in the presence of a base, e.g. imidazole. The halo-containing product can then be isolated and purified in a conventional manner.

Pharmaceutically acceptable acid addition salts of the compounds of the formula (I) are those formed from strong acids which form non-toxic acid addition salts, such as hydrochloric, hydrobromic, sulphuric, oxalic and methanesulphonic acids. Such salts are also useful for agricultural use.

The salts may be obtained by conventional procedures, e.g. by mixing solutions containing approximately equimolar amounts of the free base and desired acid, and the required salt is collected by filtration, if insoluble, or by evaporation of the solvent.

The compounds of the formula (I) and salts are antifungal agents, useful in combating fungal infections in animals, including humans. For example they are useful in treating topical fungal infections in man caused by among other organisms, species of Candida, Trichophyton, Microsporum or Epidermophyton, or in mucosal infections caused by *Candida albicans* (e.g. thrush and vaginal candidiasis). They can also be used in the treatment of systemic fungal infections caused by, for example, *Candida albicans, Cryptococcus neoformans, Aspergillus flavus, Aspergillus funigatus,* Coccidiodies, Paracoccidioides, Histoplasma or Blastomyces.

The in vitro evaluation of the antifungal activity of the compounds can be performed by determining the minimum inhibitory concentration (m.i.c.) which is the concentration of the test compounds, in a suitable medium, at which growth of the particular microorganism fails to occur. In practice, a series of agar plates, each having the test compound incorporated at a particular concentration is inoculated with a standard culture of, for example, *Candida albicans* and each plate is then incubated for 48 hours at 37° C. The plates are then examined for the presence or absence of growth of the fungus and the appropriate m.i.c. value is noted. Other micro-organisms used in such tests can include *Candida albicans, Aspergillus fumigatus,* Trichophyton spp; Microsporum spp; *Epidermophyton floccosum, Coccidioides immitis* and *Torulopsis glabrata*.

The in vivo evaluation of the compounds can be carried out at a series of dose levels by intraperitoneal or intravenous injection or by oral administration, to mice which are inoculated with, e.g., a strain of *Candida albicans* or *Aspergillus flavus*. Activity is based on the survival of a treated group of mice after the death of an untreated group of mice. The dose level at which the compound provides 50% protection against the lethal effect of the infection ($PD_{50}$) is noted.

For human use, the antifungal compounds of the formula (I) and their salts can be administered alone, but will generally be administered in admixture with a pharmaceutical carrier selected with regard to the intended route of administration and standard pharmaceutical practice. For example, they can be administered orally in the form of tablets containing such excipients as starch or lactose, or in capsules or ovules either alone or in admixture with excipients, or in the form of elixirs or suspensions containing flavouring or colouring agents. They can be injected parenterally, for example, intravenously, intramuscularly or subcutaneously. For parenteral administration, they are best used in the form of a sterile aqueous solution which may contain other substances, for example, enough salts or glucose to make the solution isotonic with blood.

For oral and parenteral administration to human patients, the daily dosage level of the antifungal compounds of the formula (I) and their salts will be from 0.1 to 10 mg/kg (in divided doses) when administered by either the oral or parenteral route. Thus tablets or capsules of the compounds will contain from 5 mg. to 0.5 g of active compound for administration singly or two or more at a time as appropriate. The physician in any event will determine the actual dosage which will be most suitable for an individual patient and it will vary with the age, weight and response of the particular patient. The above dosages are exemplary of the average case; there can, of course, be individual instances where higher or lower dosage ranges are merited, and such are within the scope of this invention.

Alternatively, the antifungal compounds of formula (I) can be administered in the form of a suppository or pessary, or they may be applied topically in the form of a lotion, solution, cream, ointment or dusting powder. For example, they can be incorporated into a cream consisting of an aqueous emulsion of polyethylene glycols or liquid paraffin; or they can be incorporated, at a concentration between 1 and 10%, into an ointment consisting of a white wax or white soft paraffin base together with such stabilizers and preservatives as may be required.

The compounds of the formula (I) and salts also have activity against a variety of plant pathogenic fungi, including for example various rusts, mildews and moulds, and the compounds are thus useful for treating plants and seeds to eradicate or prevent such diseases.

The in vitro evaluation of the activity of the compounds against plant fungi can be determined by measuring their minimum inhibitory concentrations in the same way as previously described except that the plates are incubated at 30° C. for 48 hours or longer before being examined for the presence or absence of growth.

Micro-organisms used in such tests include *Cochliobolus carbonum, Pyricularia oryzae, Glomerella cingulata, Penicillium digitatum, Botrytis cinerea* and *Rhizoctonia solani.*

For agricultural and horticultural purposes the compounds and their agriculturally acceptable salts are preferably used in the form of a composition formulated as appropriate to the particular use and purpose desired. Thus the compounds may be applied in the form of dusting powders, or granules, seed dressings, aqueous solutions, dispersions or emulsions, dips, sprays, aerosols or smokes. Compositions may also be supplied in the form of dispersible powders, granules or grains, or concentrates for dilution prior to use. Such compositions may contain such conventional carriers, diluents or adjuvants as are known and acceptable in agriculture and horticulture and they are manufactured in accordance with conventional procedures. The compositions may also incorporate other active ingredients, for example, compounds having herbicidal or insecticidal activity or a further fungicide. The compounds and compositions can be applied in a number of ways, for example they can be applied directly to the plant foliage, stems, branches, seeds or roots or to the soil or other growing medium, and they may be used not only to eradicate disease, but also prophylactically to protect the plants or seeds from attack. Most preferably, the compositions contain from 0.01 to 1 wt.% of the active ingredient. For field use, likely application rates of the active ingredient are from 5 to 500 g/10 ares.

The following Examples illustrate the invention. All temperatures are in °C. Two p.s.i. is equivalent to $1.38 \times 10^4$ pascals.

EXAMPLE 1

1-(2,4-Dichlorophenyl)-1-[1H-1,2,4-triazol-1-yl]cyclopropyl)-2-(1H-1,2,4-triazol-1-yl)ethanol

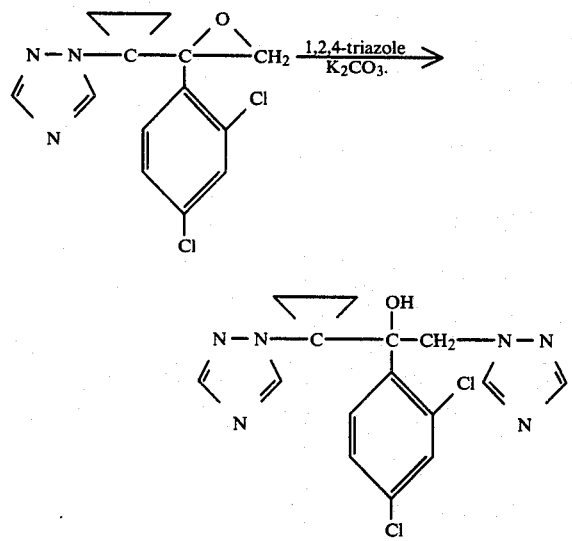

To a solution of 2-(2,4-dichlorophenyl)-2-(1-[1H-1,2,4-triazol-1-yl]cyclopropyl)oxirane (0.5 g, 1.7 mMole) in dimethylformamide (5 ml) was added 1,2,4-triazole (0.23 g, 3.4 mMole) and anhydrous potassium carbonate (0.23 g, 1.7 mMole). Heating to 85° was carried out, with stirring, for 2 hours. The solvent was then evaporated, being replaced with water (10 ml). An extraction with methylene chloride (3×10 ml) was carried out and the combined organic extracts were washed with water (3×10 ml) and dried over anhydrous magnesium sulphate. The dried solution was then evaporated to a gum, weight 0.46 g.

Purification was carried out by 'flash' column chromatography under slight pressure (2 p.s.i.) on a Merck "Kieselgel 60" (trade mark) 230–400 mesh silica-packed column, eluting with methanol and methylene chloride.

The appropriate fractions after collection and evaporation gave a solid which was recrystallised from cyclohexane and ethyl acetate to give the pure title compound, 0.12 g, m.p. 146°–147° (19.2% yield).

Analysis %: Calculated for $C_{15}H_{14}Cl_2N_6O$: C, 49.3; H, 3.9; N, 23.0; Found: C, 49.0; H, 3.8; N, 22.7.

N.m.r. and mass spectral data for the product were consistent with the stated structure.

EXAMPLES 2–4

The following compounds were prepared similarly to the preceding Example from the appropriate oxirane, 1,2,4-triazole and potassium carbonate:

| Example No. | R | m.p. (°C.) and yield | Analysis % |
|---|---|---|---|
| 2 | 2,4-difluorophenyl | 154–154° (yield 57%) | Calculated for $C_{15}H_{14}F_2N_6O$: C, 54.2; H, 4.2; N, 25.3; Found: C, 53.9; H, 4.3; N.25.1. |
| 3 | 4-chlorophenyl | 209–211° (yield 25.3%) | Calculated for $C_{15}H_{15}ClN_6O$: C, 54.5; H, 4.6; N, 25.4; Found: C, 54.5; H, 4.5; N, 25.1. |
| 4 | 4-fluorophenyl | 169–172° (yield 24%) | Calculated for $C_{15}H_{15}FN_6O$: C, 57.4; H, 4.8; N, 26.7; Found: C, 57.7; H, 4.8; N, 26.8. |

EXAMPLE 5

1-Chloro-1-(4-fluorophenyl)-1-(1-[1H-1,2,4-triazol-1-yl]cyclopropyl)-2-(1H-1,2,4-triazol-1-yl)ethane ¼hydrate

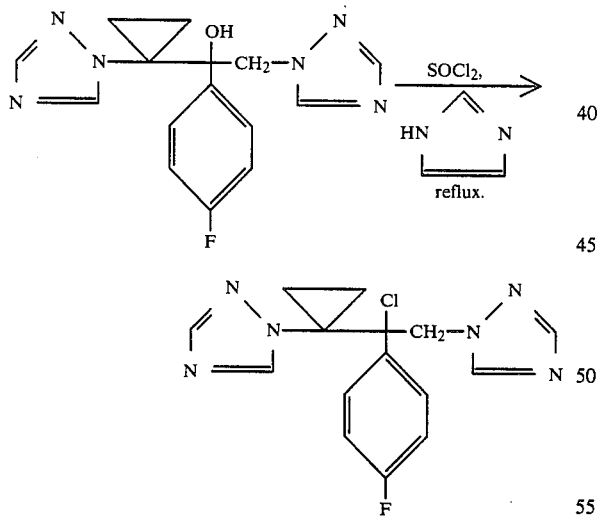

A solution of imidazole (0.27 g) in dry acetonitrile (5 ml) was treated with thionyl chloride (0.17 ml) and then 1-(4-fluorophenyl)-1-(1-[1H-1,2,4-triazol-1-yl]cyclopropyl)-2-(1H-1,2,4-triazol-1-71)ethanol (0.26 g) (product of Example 4). The resulting mixture was heated to reflux for 2 hours, and the solvent removed in vacuo. The residual oil was partitioned between ethyl acetate (50 ml) and saturated aqueous sodium bicarbonate (50 ml), and the two phases separated. The organic phase was washed with saturated brine and dried over MgSO₄. Evaporation of the solvent in vacuo gave an oil which was purified by flash chromatography on silica (50 g, 230–400 mesh), eluting with 95% ethyl acetate/5% diethylamine. Trituration with hexane gave the title compound, (64 mg, 24%), m.p. 81°–4°.

Analysis %: Found: C, 53.27; H, 4.32; N, 24.99; Calculated for $C_{15}H_{14}ClFN_6.\frac{1}{4}H_2O$: C, 53.36; H, 4.30; N, 24.90.

N.M.R., i.r. and mass spectral analysis confirmed the stated structure.

EXAMPLE 6

By a procedure similar to that of Example 5, 1-chloro-1-(4-chlorophenyl)-1-(1-[1H-1,2,4-triazol-1-yl]cyclopropyl)-2-(1H-1,2,4-triazol-1-yl)ethane hemihydrate was prepared from thionyl chloride, imidazole and the appropriate ethanol derivative. Evaporation of eluate after chromatography gave a gum which slowly crystallised on standing in diethylether. Recrystallisation from ethyl acetate and then isopropyl alcohol gave white crystals of the product, m.p. 100°–1° (25% yield).

Analysis %: Found: C, 50.25; H, 4.46; N, 23.62; Calculated for $C_{15}H_{14}Cl_2N_6.\frac{1}{4}H_2O$: C, 50.24; H, 419; N, 23.45.

N.m.r., i.r. and mass spectral data were consistent with the stated structure.

The following Preparations, in which all temperatures are in °C., illustrate the preparation of certain starting materials.

PREPARATION 1

(A)

2',4'-Dichloro-2-(1H-1,2,4-triazol-1-yl)propiophenone hydrochloride

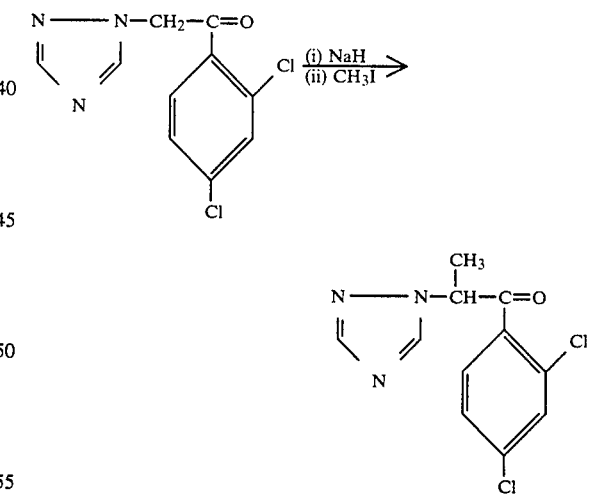

Alkylation of 2',4'-dichloro-2-(1H-1,2,4-triazol-1-yl)acetophenone (8.64 g) with methyl iodide (5.27 g) in the presence of sodium hydride (as a 50% dispersion in oil, total weight of dispersion 1.78 g) in tetrahydrofuran (150 ml) at 0° over 2 hours, yielded the title compound which was isolated as a hydrochloride salt, m.p. 125°–129°, 3.17 g, (yield 34.8%).

Analysis %: Calculated for $C_{11}H_9Cl_2N_3O.HCl$: C, 43.1; H, 3.3; N, 13.7; Found: C, 43.1; H, 3.3; N, 13.9.

N.m.r. and mass spectral data for the product were consistent with the stated structure.

(B)
2',4'-Dichloro-2-phenylselenenyl-2-(1H-1,2,4-triazol-1-yl)propiophenone

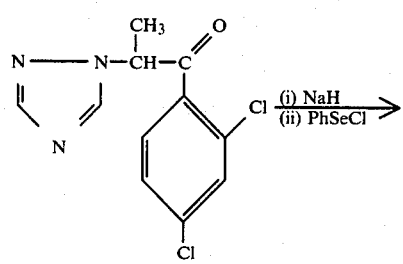

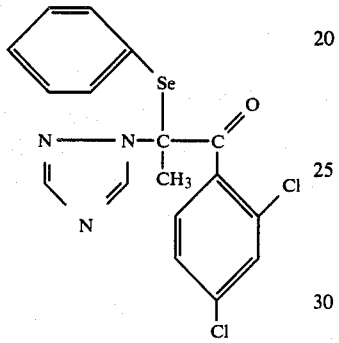

To a solution of 2',4'-dichloro-2-(1H-1,2,4-triazol-1-yl)propiophenone (3 g, 11 mMole) in tetrahydrofuran (60 ml) cooled to 5° was added sodium hydride as a 50% by weight dispersion in oil (0.68 g of said dispersion which contained 14 mMole of sodium hydride). Thirty minutes later phenylselenenyl chloride was added in four equal portions over five minutes (2.95 g, 15.4 mMole). Fifteen minutes later glacial acetic acid was added (1.5 ml) and the mixture was poured into water (100 ml). Excess solid sodium bicarbonate was added to basify the solution, which was then extracted with ethyl acetate (3×50 ml). The organic extracts were combined, washed with saturated saline solution (3×50 ml) and dried over anhydrous magnesium sulphate. Evaporation gave an impure oil, weight 5.4 g. Purification was carried out by 'flash' column chromatography under slight pressure (2 p.s.i.) on a 'Merck Kieselgel 60' (trade mark) 230–400 mesh silica-packed column, eluting with ether and 40°–60° petrol (1:1). The appropriate fractions after collection and evaporation gave a solid which was recrystallized from cyclohexane to give the pure title compound, 2.57 g, m.p. 84°–86° (47% yield).

Analysis %: Calculated for $C_{17}H_{13}Cl_2N_3OSe$: C, 48.0; H, 3.1; N, 9.9; Found: 3,48.0; H, 3.2; N, 10.2.

N.m.r., i.r. and mass spectral data for the product were consistent with the stated structure.

(C)
2',4'-Dichloro-2-(1H-1,2,4-triazol-1-yl)prop-2-enophenone

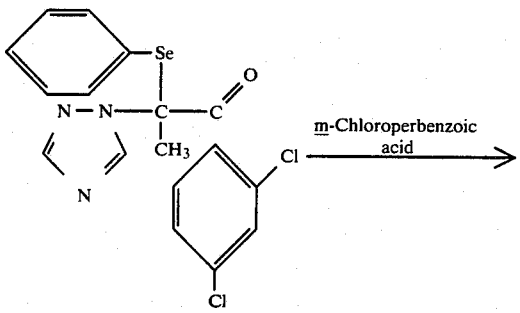

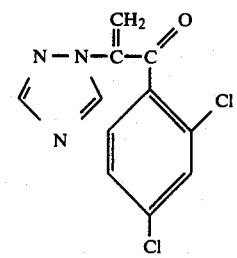

To a solution of the product of Part (B) (0.42 g, 1.0 mMole) in methylene chloride (5 ml) at −72° was added m-chloroperbenzoic acid (0.32 g, 1.5 mMole) in three equal portions over a twelve minute period. Two hours later the mixture, at −70°, was poured into an aqueous solution of saturated sodium bicarbonate and sodium sulphite (20 ml) with vigorous stirring. The organic layer was separated, washed with saturated sodium bicarbonate (3×5 ml) and water (3×5 ml), and dried over anhydrous sodium sulphate. Evaporation gave the title compound as an oil, 0.20 g, (74% yield). The compound was used directly in the next stage.

(D)
1-(1H-1,2,4-Triazol-1-yl)cyclopropyl 2,4-dichlorophenyl ketone

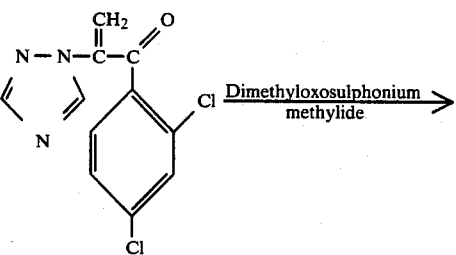

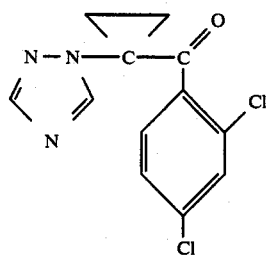

2',4'-Dichloro-2-(1H-1,2,4-triazol-1-yl)prop-2-enophenone (0.27 g, 1.0 mMole) was added dropwise in 1,1,1-trichloroethane (2 ml) to a refluxing mixture of trimethylsulphoxonium iodide (0.33 g, 1.5 mMole), cetrimide (0.03 g), 1,1-trichloroethane (5 ml) and aqueous 2N sodium hydroxide (3 ml) with vigorous stirring over 2 minutes. After refluxing for a further 15 minutes the organic phase, after cooling, was separated. Evaporation gave a gum, weight 0.11 g.

Purification was carried out by 'flash' column chromatography on 'Merck Kieselgel 60' (trade mark) 230–400 mesh silica, eluting with ether.

The appropriate fractions after collection and evaporation gave the pure title compound as a gum, 0.051 g, (18% yield).

N.m.r. and mass spectral data for product were consistent with the stated structure.

N.m.r. (CDCl$_3$). $\delta$=1.85 (m, 2H0, 2.1 (m, 2H), 7.1–7.25 (m, 3H), 7.8 (s, 1H), 8.15 (s, 1H).

Analysis %: Calculated for $C_{12}H_9Cl_2N_3O$: C, 51.1; H, 3.2; N, 14.9; Found: C, 50.8; H, 3.0; N, 15.0.

(E)
2-(2,4-Dichlorophenyl)-2-[1-(1H-1,2,4-triazol-1-yl)cyclopropyl]oxirane

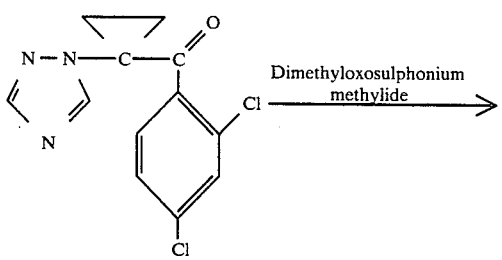

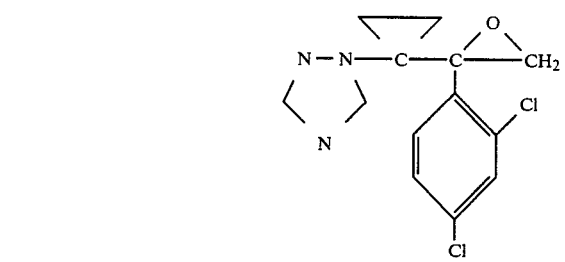

1-(1-H-1,2,4-Triazol-1-yl)cyclopropyl 2,4-dichlorophenyl ketone (0.5 g, 1.8 mMole) was added to trimethylsulfphoxonium iodide (0.57 g, 2.6 mMole), cetrimide (0.02 g), 1,1,1-trichloroethane (10 ml) and aqueous sodium hydroxide solution (5 ml of 20%). The mixture was refluxed for twenty hours.

The organic phase was then separated and the aqueous phase was extracted with methylene chloride (3×10 ml).

The organic extracts were combined with the organic phase and washed with saturated saline (3×10 ml) followed by drying over anhydrous magnesium sulphate. Evaporation gave the title compound as an oil, 0.28 g, (52.5% yield).

N.m.r. and mass spectra data for the product were consistent with the stated structure.

mass spec. M-1=294; M-29=265; M-30-35=230; for $C_{13}H_{11}Cl_2N_3O$ M-35=259.

PREPARATION 2

[Alternative to Preparation 1 Parts (A) to (D)]

1-(1H-1,2,4-Triazol-1-yl)cyclopropyl 2,4-dichlorophenyl ketone

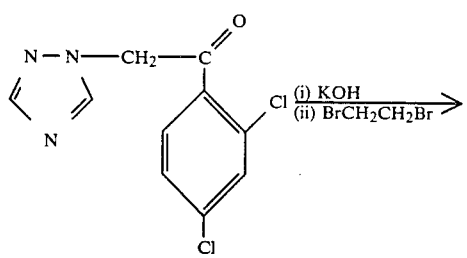

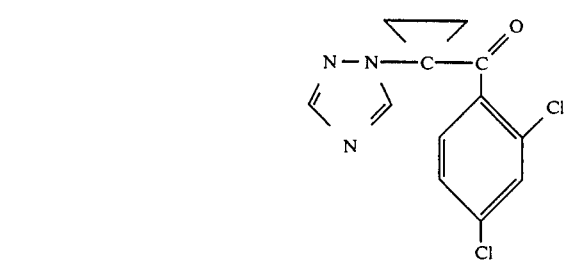

Potassium hydroxide (4.88 g, 88 mMole) was added to solution of 2-(1H-1,2,4-triazol-1-yl)-2',4'-dichloroacetophenone (see British Patent Application Publication No. 2078719A) (10.24 g, 40 mMole) in diemthylsulphoxide (100 ml). Thirty minutes later 1,2-dibromoethane was added in one batch (8.28 g, 44 mMole) with stirring.

Stirring was continued for 20 hours.

The mixture was then poured into water (175 ml) and extracted with methylene chloride (3×50 ml). The organic extracts were combined and washed with water (3×50 ml).

The solution was dried over anhydrous magnesium sulphate and evaporated to a gum, weight 11.92 g. Purification was carried out by 'flash' column chromatography under slight pressure (2 p.s.i.) on a Merck "Kieselgel 60" (trade mark) 230–400 mesh silica-packed column, eluting with ether.

The appropriate fractions after collection and evaporation gave a gum which solidified on standing to give the pure title compound, 2.51 g, m.p. 55°–56° (22.2% yield)

N.m.r. and mass spectral data for the product were consisting with the stated structure. The compound was confirmed spectroscopically to be identical to the product of Preparation 1(D).

PREPARATION 3

1-(1H-1,2,4-triazol-1-yl)cyclopropyl 4-fluorophenyl ketone

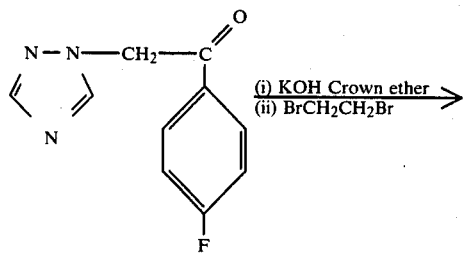

(i) KOH Crown ether
(ii) BrCH₂CH₂Br

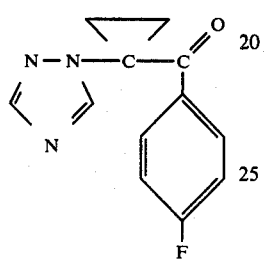

To a solution of 2-(1H-1,2,4-triazol-1-yl)-4'-fluoroacetophenone (10.24 g, 50 mMole) in methylene chloride (70 ml) was added 18-Crown-6 ether (1 g) (trade mark for 1,4,7,10,13,16-hexaoxacyclooctadecane) and potassium hydroxide (6.1 g, 109 mMole) with stirring. Ten minutes later 1,2-dibromoethane was added (10.3 g, 55 mMole in one batch. Stirring was continued for 18 hours. The mixture was poured into saturated saline solution (100 ml) and the organic phase was separated, washed with water (3×30 ml) and dried over anhydrous magnesium sulphate. Evaporation gave an oil, weight 13.7 g. Purification was carried out by flash column chromatography under slight pressure (2 p.s.i.) on a Merck "Kieselgel 60" (trade mark) 230–400 mesh fractions after collection and evaporation gave a solid, the pure title compound, 2.9 g, m.p. 73°–75° (25% yield).

Analysis %: Calculated for C₁₂H₁₀FN₃O: C, 62.3; H, 4.5; N, 18.3; Found: C, 62.3; H, 4.4; N, 18.2.

N.m.r., i.r. and mass spectral data for the product were consistent with the stated structure.

2-(1H-1,2,4-Triazol-1-yl)-4'-fluoroacetophenone was prepared by procedures analogous to those described in GB 2078719A.

PREPARATIONS 4 AND 5

The following ketones were prepared similar to the method of the preceding Preparation from the appropriate starting materials.

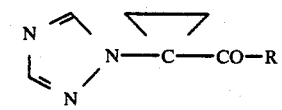

| Preparation No. | R | m.p. (°C.) and yield | Analysis |
|---|---|---|---|
| 4 | 4-fluorophenyl (F at para) | 89–90° (yield 23.3%) | Calcd. for C₁₂H₉F₂N₃O: C, 57.8; H, 3.5; N, 16.9; Found: C, 57.9; H, 3.6; N, 16.6. |
| 5 | 4-chlorophenyl | 88–90° (yield 25.4%) | Calcd. for C₁₂H₁₀ClN₃O: C, 58.2; H, 4.0; N, 17.0; Found: C, 58.3; H, 4.0; N, 17.0. |

The preparation of the starting material 2-(1H-1,2,4-triazol-1-yl)-2',4'-difluoroacetophenone is described in European patent application publication no. 69442. 2-(1H-1,2,4-Triazol-1-yl)-4'-chloroacetophenone was prepared similarly.

PREPARATION 6

The following epoxides were prepared similarly to the method of Preparation 1(E) using the appropriate ketone, trimethylsulphoxonium iodide, cetrimide and aqueous sodium hydroxide:

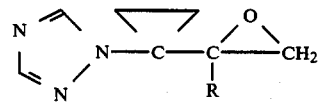

R=4-fluorophenyl; 2,4-difluorophenyl and 4-chlorophenyl.

The epoxides were characterized by n.m.r. and i.r. spectral data.

ACTIVITY DATA

The compounds of the formula (I) have the following PD₅₀ values (mg./kg., oral) in mice after 48 hours when measured by the method previously described:

| Compound | PD₅₀(mg./kg.) |
|---|---|
| Product of Example 1 | <1.0 |
| Product of Example 2 | <1.0 |
| Product of Example 3 | <1.0 |
| Product of Example 4 | <1.0 |
| Product of Example 5 | 3.0 |
| Product of Example 6 | 1.6 |

We claim:
1. A compound of the formula

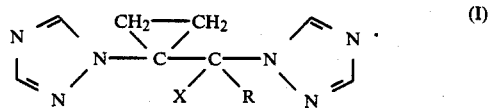

(I)

and a pharmaceutically or agriculturally acceptable salt thereof, wherein X is selected from the group consisting of hydroxy and chloro; and R is selected from the group consisting of chlorophenyl, fluorophenyl, dichlorophenyl, difluorophenyl and 5-chloropyrid-2-yl.

2. A compound of claim 1, wherein X is hydroxy.

3. The compound of claim 2, wherein R is 2,4-dichlorophenyl.

4. The compound of claim 2, wherein R is 2,4-difluorophenyl.

5. The compound of claim 2, wherein R is 4-chlorophenyl.

6. The compound of claim 2, wherein R is 4-fluorophenyl.

7. A pharmaceutical composition comprising a compound according to claim 1 or a pharmaceutically acceptable salt thereof together with a pharmaceutically acceptable diluent or carrier.

8. A fungicidal composition for agricultural use comprising a compound according to claim 1 or an agriculturally acceptable salt thereof together with an agriculturally acceptable diluent or carrier.

9. A method of treating a plant or seed having a fungal infection, which comprises treating said plant or seed with an antifungally effective amount of a composition according to claim 8.

10. A method of treating a fungal infection in a human being, which comprises administering to said human being an antifungally effective amount of a composition according to claim 7.

* * * * *

UNITED STATES PATENT AND TRADEMARK OFFICE
CERTIFICATE OF CORRECTION

PATENT NO. : 4,618,616

DATED : October 21, 1986

INVENTOR(S) : Kenneth Richardson, et al.

It is certified that error appears in the above-identified patent and that said Letters Patent is hereby corrected as shown below:

Col. 1, formula (I) should read

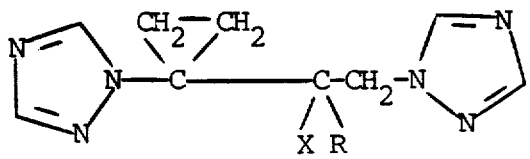

Col. 14, claim 1, formula (I) should read

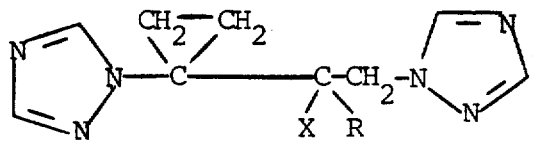

Signed and Sealed this

Fourteenth Day of April, 1987

Attest:

DONALD J. QUIGG

Attesting Officer

Commissioner of Patents and Trademarks

Notice of Adverse Decision in Interference

In Interference No. 101,841, involving Patent No. 4,618,616, K. Richardson, R. J. Bass and K. Cooper, CYCLOPROPYLIDENE ANTIFUNGAL AGENTS, final judgment adverse to the patentees was rendered Dec. 7, 1988, as to claims 1 - 10.

[*Official Gazette February 14, 1989.*]

Notice of Adverse Decision in Interference

In Interference No. 102,043, involving Patent No. 4,618,616, K. Richardson, R. J. Bass and K. Cooper, CYCLOPROPYLIDENE ANTIFUNGAL AGENTS, final judgment adverse to the patentees was rendered Sept. 28, 1989 as to claim 10.

[*Official Gazette November 21, 1989*]